US010092039B2

(12) United States Patent
Bless et al.

(10) Patent No.: US 10,092,039 B2
(45) Date of Patent: Oct. 9, 2018

(54) SMOKING ARTICLE FOR ON-DEMAND DELIVERY OF AN INCREASED QUANTITY OF AN AEROSOL PRECURSOR COMPOSITION, A CARTRIDGE, AND A RELATED METHOD

(71) Applicant: RAI Strategic Holdings, Inc., Winston-Salem, NC (US)

(72) Inventors: Alfred Charles Bless, Asheboro, NC (US); Charles Jacob Novak, III, Winston-Salem, NC (US); Stephen Benson Sears, Siler City, NC (US); Joseph Dominique, Winston-Salem, NC (US); Jared Aller, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 15/378,772

(22) Filed: Dec. 14, 2016

(65) Prior Publication Data

US 2018/0160732 A1 Jun. 14, 2018

(51) Int. Cl.
*A24F 47/00* (2006.01)
*A61M 11/00* (2006.01)
*H05B 1/02* (2006.01)

(52) U.S. Cl.
CPC ......... *A24F 47/008* (2013.01); *H05B 1/0244* (2013.01); *H05B 2203/021* (2013.01)

(58) Field of Classification Search
CPC ........... H05B 1/0244; H05B 2203/021; A61M 15/025; A61M 11/007; A24F 47/002; A24F 47/008
See application file for complete search history.

(56) References Cited

U.S. PATENT DOCUMENTS 4,735,217 A 4/1988 Gerth et al.
4,793,365 A 12/1988 Sensabaugh et al.
(Continued)

FOREIGN PATENT DOCUMENTS

EP 3 061 357 8/2016
EP 3 100 621 12/2016
(Continued)

OTHER PUBLICATIONS

Chemical and Biological Studies on New Cigarette Prototypes that Heat Instead of Burn Tobacco, R. J. Reynolds Tobacco Company Monograph (1988).

*Primary Examiner* — Briggitte R Hammond
(74) *Attorney, Agent, or Firm* — Womble Bond Dickinson (US) LLP

(57) ABSTRACT

A smoking article for on-demand delivery of an increased quantity of an aerosol precursor composition, a cartridge, and a method are disclosed. In some aspects, the cartridge includes a housing, and a reservoir disposed within the housing and defining two or more chambers each having an aerosol precursor composition therein. The reservoir is in fluid communication with an aerosol forming arrangement configured to form an aerosol from any of the aerosol precursor compositions, with the respective aerosol precursor compositions of the two or more chambers being directed to the aerosol forming arrangement in substantially equal normal quantities. The cartridge further includes an actuator configured to selectively and operably engage any one of the chambers and to direct an increased quantity of the aerosol precursor composition from the chamber engaged therewith to the aerosol forming arrangement, the increased quantity being greater than the normal quantity of the aerosol precursor compositions.

43 Claims, 7 Drawing Sheets

(56) References Cited

U.S. PATENT DOCUMENTS 4,922,901 A 5/1990 Brooks et al.
4,947,874 A 8/1990 Brooks et al.
4,947,875 A 8/1990 Brooks et al.
5,060,671 A 10/1991 Counts et al.
5,093,894 A 3/1992 Deevi et al.
5,101,839 A 4/1992 Jakob et al.
5,224,498 A 7/1993 Deevi et al.
5,228,460 A 7/1993 Sprinkel et al.
5,249,586 A 10/1993 Morgan et al.
5,261,424 A 11/1993 Sprinkel, Jr. et al.
5,322,075 A 6/1994 Deevi et al.
5,353,813 A 10/1994 Deevi et al.
5,372,148 A 12/1994 McCafferty et al.
5,468,936 A 11/1995 Deevi et al.
5,498,850 A 3/1996 Das
5,498,855 A 3/1996 Deevi et al.
5,530,225 A 6/1996 Hajaligol
5,573,692 A 11/1996 Das et al.
5,591,368 A 1/1997 Fleischhauer et al.
5,659,656 A 8/1997 Das
5,665,262 A 9/1997 Hajaligol et al.
5,666,977 A 9/1997 Higgins et al.
5,934,289 A 8/1999 Watkins et al.
5,954,979 A 9/1999 Counts et al.
5,967,148 A 10/1999 Harris et al.
6,040,560 A 3/2000 Fleischhauer et al.
6,053,176 A 4/2000 Adams et al.
6,164,287 A 12/2000 White
6,196,218 B1 3/2001 Voges
6,772,756 B2 8/2004 Shayan
6,803,545 B2 10/2004 Blake et al.
6,810,883 B2 11/2004 Felter et al.
6,854,461 B2 2/2005 Nichols et al.
7,040,314 B2 5/2006 Nguyen et al.
7,293,565 B2 11/2007 Griffin et al.
7,513,253 B2 4/2009 Kobayashi et al.
7,726,320 B2 6/2010 Robinson et al.
7,832,410 B2 11/2010 Hon
7,896,006 B2 3/2011 Hamano et al.
8,156,944 B2 4/2012 Han
8,375,957 B2 2/2013 Hon
8,402,976 B2 3/2013 Fernando et al.
8,689,804 B2 4/2014 Fernando et al.
8,794,231 B2 8/2014 Thorens et al.
8,851,083 B2 10/2014 Oglesby et al.
8,881,737 B2 11/2014 Collett et al.
8,910,639 B2 12/2014 Chang et al.
8,915,254 B2 * 12/2014 Monsees ............... A24F 47/006
131/194
8,925,555 B2 1/2015 Monsees et al.
9,687,027 B2 * 6/2017 Poston .................. A24F 47/008
2005/0263618 A1 12/2005 Spallek et al.
2006/0196518 A1 9/2006 Hon
2009/0188490 A1 7/2009 Han
2010/0024834 A1 2/2010 Oglesby et al.
2010/0028766 A1 2/2010 Peckerar et al.
2010/0307518 A1 12/2010 Wang
2013/0255702 A1 10/2013 Griffith, Jr. et al.
2014/0000638 A1 1/2014 Sebastian et al.
2014/0060554 A1 * 3/2014 Collett .................. A24F 47/008
131/328
2014/0096781 A1 4/2014 Sears et al.
2014/0261408 A1 * 9/2014 DePiano ............... A24F 47/008
128/202.21
2014/0261488 A1 9/2014 Tucker
2015/0020825 A1 * 1/2015 Galloway ............. A24F 47/008
131/329
2015/0117842 A1 * 4/2015 Brammer ................. H05B 3/02
392/387
2015/0201674 A1 * 7/2015 Dooly ................... A24F 47/008
53/432
2015/0226432 A1 * 8/2015 Borschke ................ F23Q 13/04
431/253
2016/0325858 A1 * 11/2016 Ampolini .............. A24F 47/008
2016/0338407 A1 * 11/2016 Kerdemelidis ....... A24F 47/008
2017/0020190 A1 * 1/2017 Chang ................... A24F 47/008

FOREIGN PATENT DOCUMENTS

WO WO 98/57556 12/1998
WO WO 2010/003480 1/2010
WO WO 2010/091593 8/2010

* cited by examiner

SMOKING ARTICLE FOR ON-DEMAND DELIVERY OF AN INCREASED QUANTITY OF AN AEROSOL PRECURSOR COMPOSITION, A CARTRIDGE, AND A RELATED METHOD

FIELD OF THE DISCLOSURE

The present disclosure relates to smoking articles and, more particularly, to a smoking article for on-demand delivery of an increased quantity of an aerosol precursor composition, a cartridge, and a related method, wherein the on-demand delivery of the increased quantity of the aerosol precursor composition is effectuated by a user-actuated actuator.

BACKGROUND

Numerous smoking products that attempt to provide the sensations of cigarette, cigar, or pipe smoking without burning tobacco to a significant degree have been developed. Of those products, many have aerosol precursor compositions that include flavor generators, vapor generators, varying nicotine contents, etc., to deliver a normal quantity of the aerosol precursor composition to an aerosol forming arrangement per individual draw on the product. See, for example, the various alternative smoking products including smoking articles, aerosol delivery devices, and/or heat generating sources set forth in the background art described in U.S. Pat. No. 7,726,320 to Robinson et al., U.S. Pat. App. Pub. No. 2013/0255702 to Griffith, Jr. et al., U.S. Pat. App. Pub. No. 2014/0000638 to Sebastian et al., U.S. Pat. No. 8,881,737 to Collett et al., and U.S. Pat. App. Pub. No. 2014/0096781 to Sears et al., which are incorporated herein by reference.

However, such smoking products do not necessarily allow a consumer of such products to selectively control an increased quantity of an aerosol precursor composition, or compositions, (i.e., a flavor charge) to be delivered to an aerosol forming arrangement. More particularly, it is not necessarily apparent in such smoking products that a consumer is able to selectively control delivery of an increased quantity of an aerosol precursor composition(s) to an aerosol forming arrangement, with the increased quantity being more than a normal quantity of the aerosol precursor composition(s) delivered to the aerosol forming arrangement, for example, on an individual draw basis. Such a smoking article that enables a consumer to selectively control an increased quantity of an aerosol precursor composition(s) can be more desirable, as an aerosol formed thereby would have increased characteristics directly relative to the increased quantity of aerosol precursor composition delivered to the aerosol forming arrangement; such increased characteristics including, for example, increased active ingredient (i.e., nicotine) content, increased flavor, increased vapor/aerosol production, etc.

Accordingly, it would be desirable to provide a smoking article, cartridge, and related method for on-demand delivery of an increased quantity of an aerosol precursor composition in order to provide a consumer with selectively enhanced characteristics of the produced vapor/aerosol.

BRIEF SUMMARY OF THE DISCLOSURE

The above and other needs are met by aspects of the present disclosure which, in one aspect, provides a smoking article including a control body; and a cartridge engaged with the control body. The cartridge comprises a housing having a proximal end and an opposing distal end engagable with the control body; a reservoir disposed within the housing and extending longitudinally from a first end disposed toward the proximal end of the housing to a second end disposed toward the distal end of the housing. The reservoir defines two or more chambers each having an aerosol precursor composition disposed therein, and is in fluid communication with an aerosol forming arrangement configured to form an aerosol from any of the aerosol precursor compositions. The respective aerosol precursor compositions of the two or more chambers are directed to the aerosol forming arrangement in substantially equal normal quantities. An actuator is engaged with the housing and is configured to selectively and operably engage any one of the two or more chambers defined by the reservoir. The actuator, upon actuation thereof, is configured to direct an increased quantity of the aerosol precursor composition from the chamber engaged therewith to the aerosol forming arrangement, wherein the increased quantity is greater than the normal quantity of the aerosol precursor composition.

Another aspect of the present disclosure provides a cartridge for a smoking article, the cartridge comprising a housing having a proximal end and an opposing distal end engagable with a control body of the smoking article. A reservoir is disposed within the housing and extends longitudinally from a first end disposed toward the proximal end of the housing to a second end disposed toward the distal end of the housing. The reservoir defines two or more chambers each having an aerosol precursor composition disposed therein, and is in fluid communication with an aerosol forming arrangement configured to form an aerosol from any of the aerosol precursor compositions. The respective aerosol precursor compositions of the two or more chambers are directed to the aerosol forming arrangement in substantially equal normal quantities. An actuator is engaged with the housing and is configured to selectively and operably engage any one of the two or more chambers defined by the reservoir. The actuator, upon actuation thereof, is configured to direct an increased quantity of the aerosol precursor composition from the chamber engaged therewith to the aerosol forming arrangement, wherein the increased quantity is greater than the normal quantity of the aerosol precursor composition.

Yet another aspect of the present disclosure provides a method for making a smoking article, wherein such a method comprises engaging a reservoir into fluid communication with an aerosol forming arrangement configured to form an aerosol from aerosol precursor compositions. The reservoir is disposed within a housing of a cartridge, and defines two or more chambers each extending longitudinally from a first end disposed toward a proximal end of the housing to a second end disposed toward a distal end of the housing. Each of the two or more chambers is configured to have an aerosol precursor composition disposed therein, and to direct the respective aerosol precursor compositions of the two or more chambers to the aerosol forming arrangement in substantially equal normal quantities. An actuator is engaged with the housing such that the actuator selectively and operably engages any one of the two or more chambers defined by the reservoir. The actuator is configured to be selectively actuatable to direct an increased quantity of the aerosol precursor composition from the chamber engaged therewith to the aerosol forming arrangement, with the increased quantity being greater than the normal quantity of the aerosol precursor composition.

Aspects of the present disclosure thus provide these and other advantages, as otherwise disclosed herein.

BRIEF DESCRIPTION OF THE FIGURES

Figure 1:
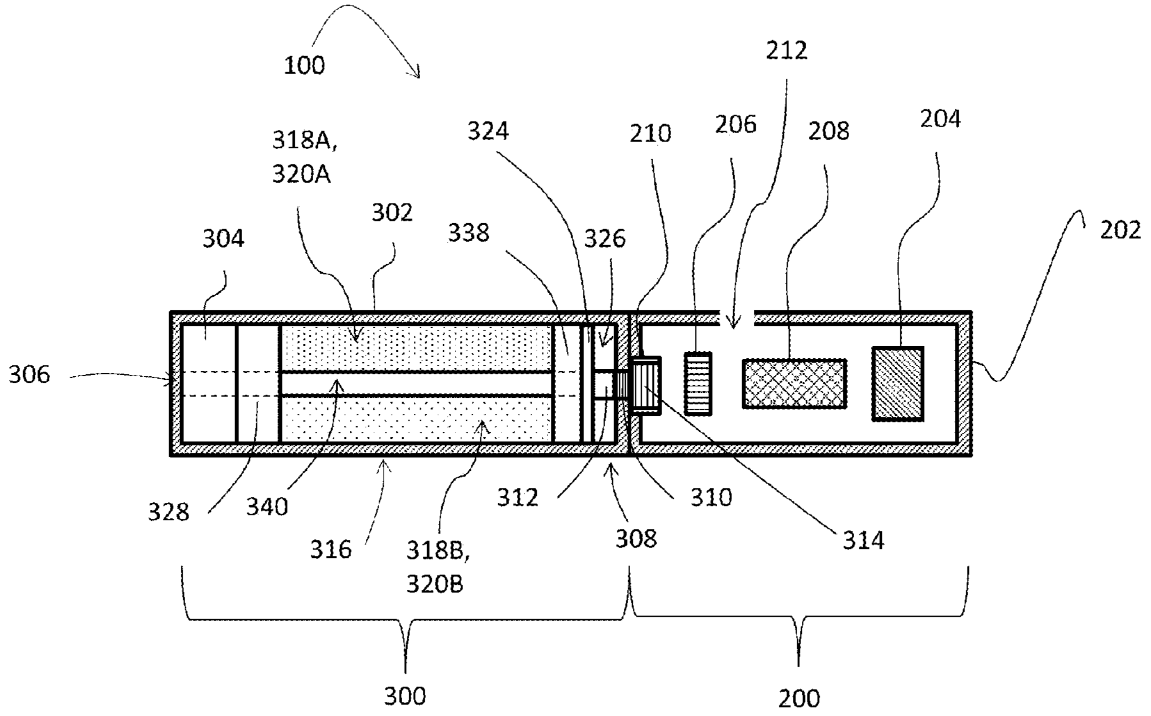
Figure 2:
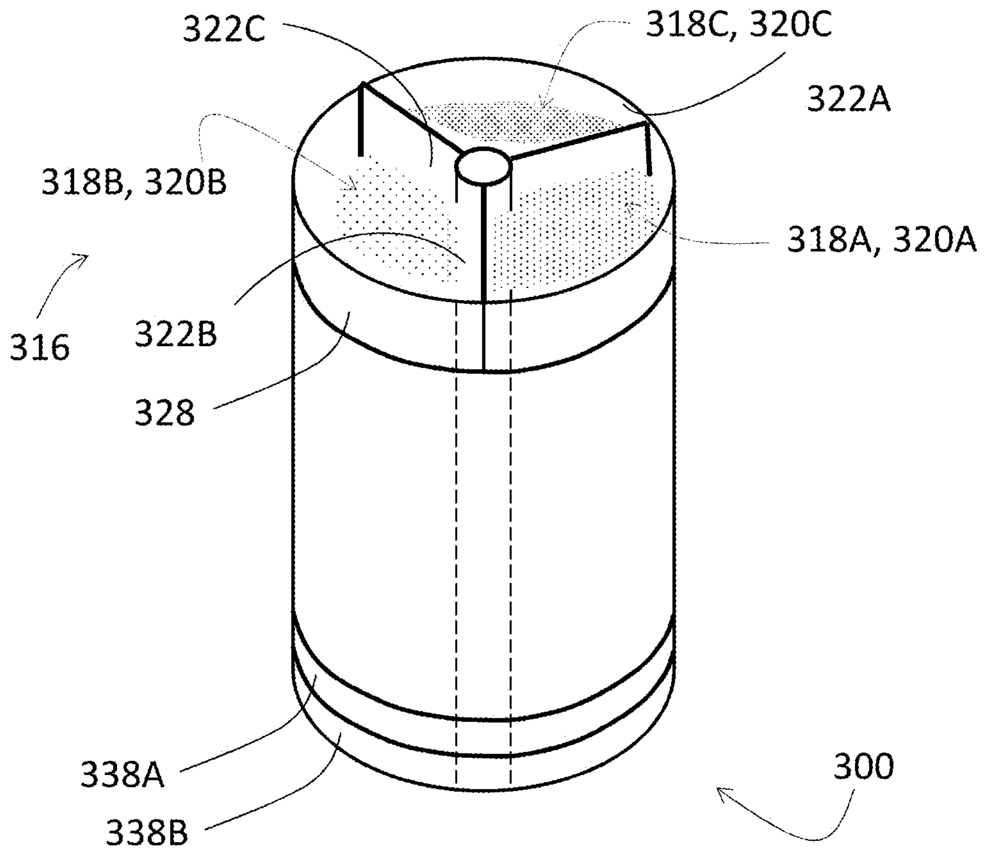
Figure 3A:
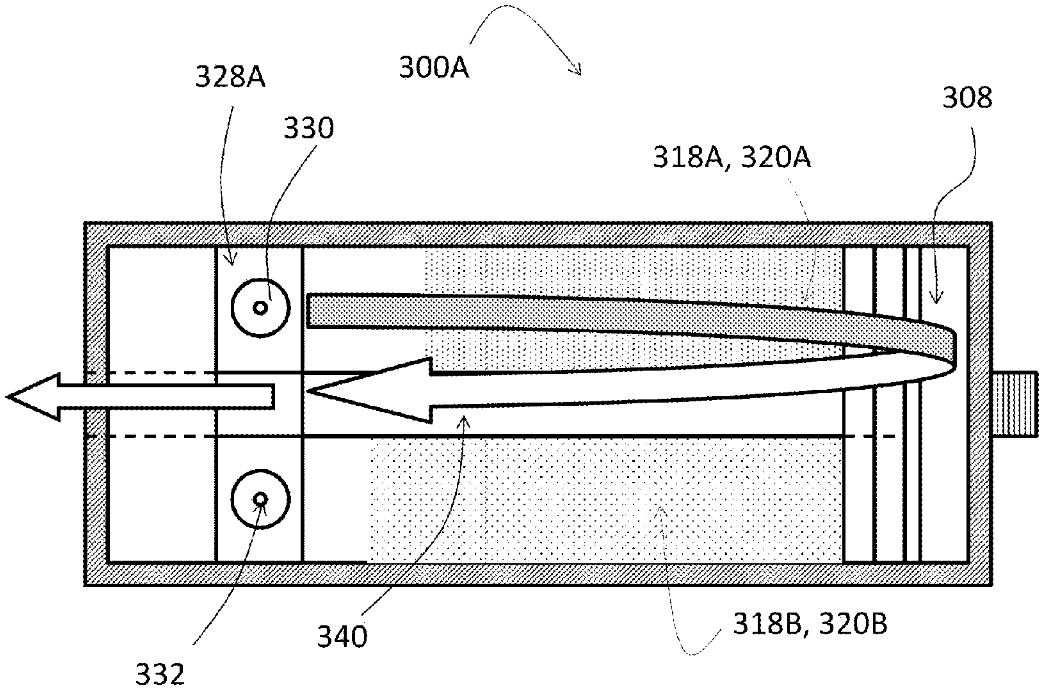
Figure 3B:
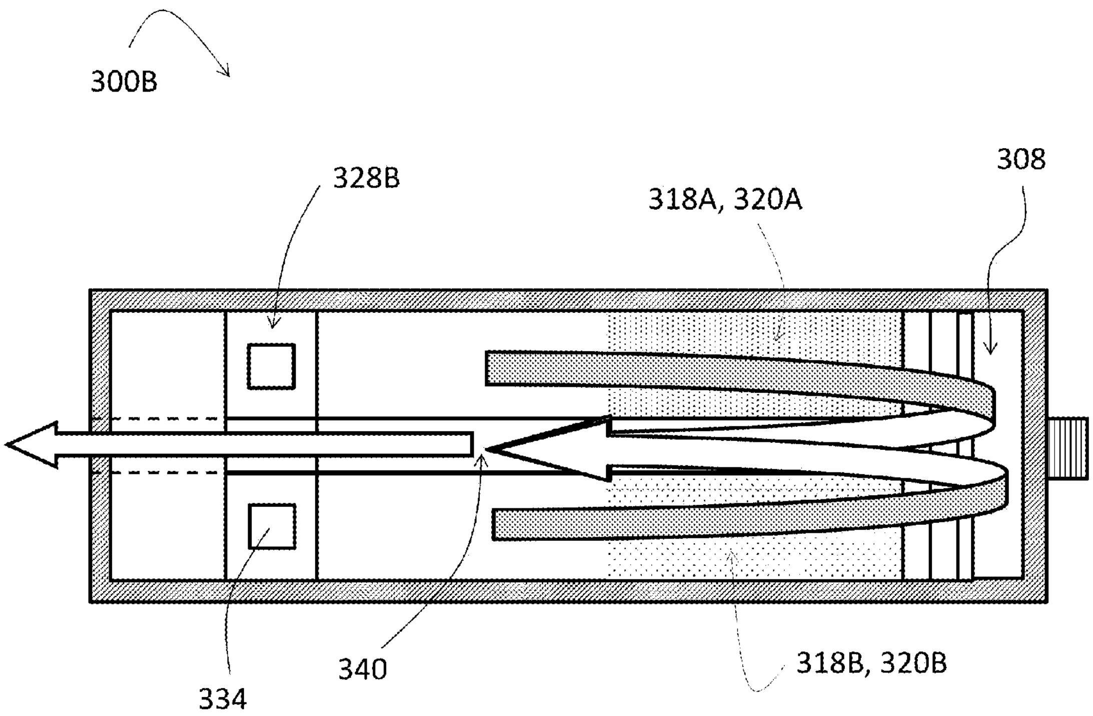
Figure 3C:
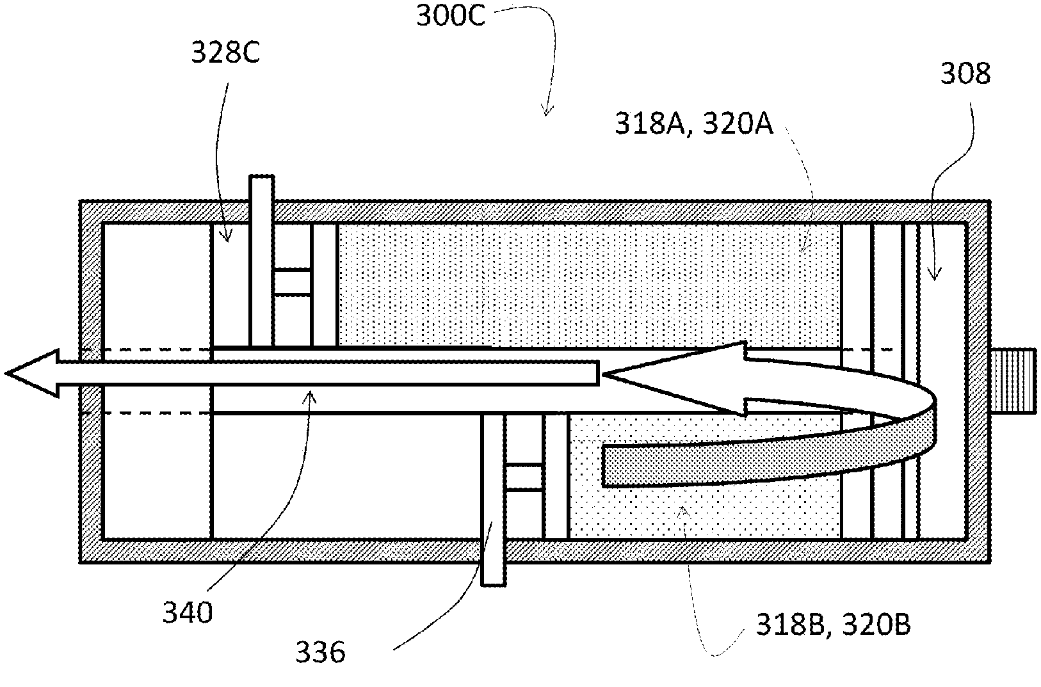
Figure 4:
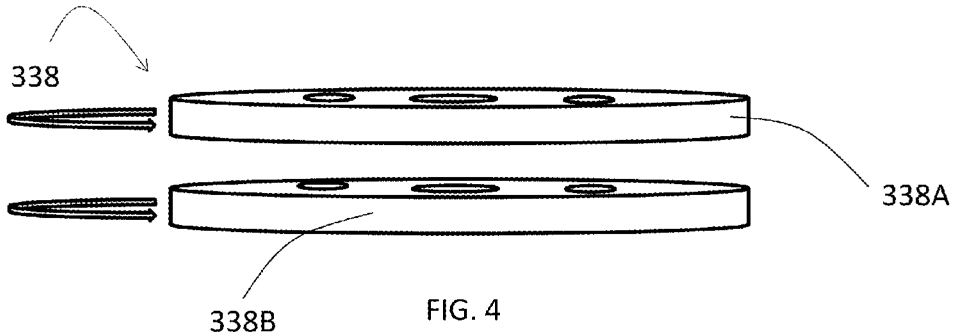
Figure 5A:
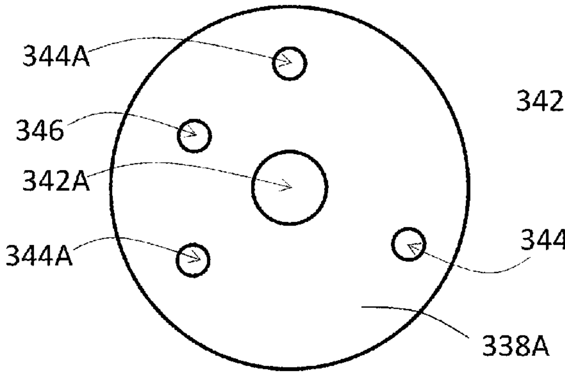
Figure 5B:
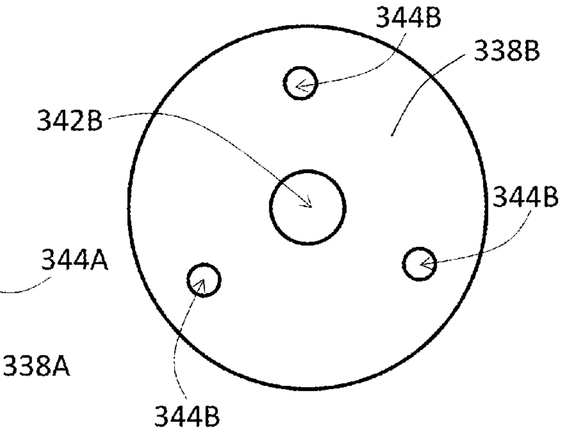
Figure 6:
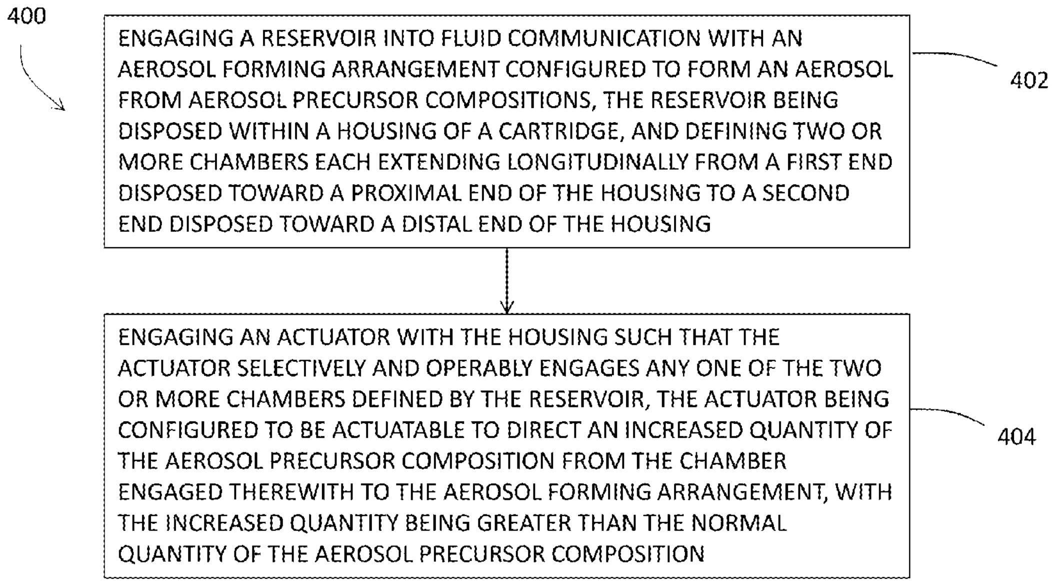

Having thus described the disclosure in the foregoing general terms, reference will now be made to the accompanying drawings, which are not necessarily drawn to scale, and wherein:

FIG. 1 illustrates a cross-sectional side view of a smoking article having a cartridge and a control body for on-demand delivery of an increased quantity of an aerosol precursor composition according to an example embodiment of the present disclosure;

FIG. 2 illustrates a perspective view of a cartridge for a smoking article, the cartridge including three chambers defined by a reservoir, according to an example embodiment of the present disclosure;

FIG. 3A illustrates a cross-sectional side view of a cartridge for a smoking article, the cartridge including a flexible bulb, according to an example embodiment of the present disclosure;

FIG. 3B illustrates a cross-sectional side view of a cartridge for a smoking article, the cartridge including a pump device, according to an example embodiment of the present disclosure;

FIG. 3C illustrates a cross-sectional side view of a cartridge for a smoking article, the cartridge including a piston mechanism, according to an example embodiment of the present disclosure;

FIG. 4 illustrates a perspective view of two aligned discs independently rotatable within a cartridge of a smoking article according to an example embodiment of the present disclosure;

FIG. 5A illustrates a top view of a first aligned disc of the two or more aligned discs of FIG. 4;

FIG. 5B illustrates a top view of a second aligned disc of the two or more aligned discs of FIG. 4; and FIG. 6 illustrates a method flow diagram of a method for making a smoking article according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of aerosol delivery devices that use electrical energy to heat a material (preferably without combusting the material to any significant degree) to form an inhalable substance (e.g., an aerosol); such devices most preferably being sufficiently compact to be considered "hand-held" devices. In certain preferred embodiments, the aerosol delivery devices can be characterized as smoking articles. As used herein, the term "smoking article" is intended to mean an article or device that provides some or all of the sensations (e.g., inhalation and exhalation rituals, types of tastes or flavors, organoleptic effects, physical feel, use rituals, visual cues such as those provided by visible aerosol (e.g., vapor), and the like) of smoking a cigarette, cigar, or pipe, without any substantial degree of combustion of any component of that article or device. As used herein, the term "smoking article" does not necessarily mean that, in operation, the article or device produces smoke in the sense of the aerosol resulting from by-products of combustion or pyrolysis of tobacco, but rather, that the article or device yields vapors (including, e.g., vapors within aerosols that can be considered to be visible aerosols that might be considered or described as smoke-like) resulting from volatilization or vaporization of certain components of the article or device. In some preferred embodiments, articles or devices characterized as smoking articles incorporate tobacco and/or components derived from tobacco.

Products or devices of the present disclosure also can be characterized as being vapor-producing articles, aerosol delivery articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, smoking articles of the present disclosure are subjected to many of the physical actions employed by an individual in using a traditional type of smoking article (e.g., a cigarette, cigar or pipe that is employed by lighting and inhaling tobacco). For example, the consumer of a smoking article of the present disclosure can hold that article much like a traditional type of smoking article, draw on one end of that article for inhalation of aerosol produced by that article, take draws at selected intervals of time, etc.

FIG. 1 illustrates an exemplary embodiment of a smoking article, generally designated 100. The smoking article 100 comprises a control body, generally designated 200, and a cartridge, generally designated 300, engaged with the control body 200. For example, the control body 200 is permanently or detachably aligned in a functioning relationship with the cartridge 300 through a threaded engagement, a press-fit engagement, interference fit, a magnetic engagement, or the like.

In specific embodiments, one or both of the control body 200 and the cartridge 300 is referred to as being disposable or as being reusable. For example, the control body 200 has a replaceable power source (e.g., battery), or is rechargeable and is thus combinable with any type of recharging technology, including connection to a typical electrical outlet, connection to a car charger (i.e., cigarette lighter receptacle), and connection to a computer, such as through a USB cable. In another example, the cartridge 300 is replaceable and disposable, or is refillable for reuse. In the exemplified embodiment, the control body 200 includes a housing 202 substantially enclosing the control body 200 within.

In one aspect, the control body 200 comprises a control component 204, a flow sensor 206, and a power source 208, which are variably aligned and in communication with each other. In some aspects, the power source 208 comprises a battery or other electrical power source for providing current flow sufficient to support various functionalities of the smoking article 100, such as resistive heating, powering of control components (e.g., control component 204), powering of indicators, and the like. Preferably, the power source 208 is sized to fit conveniently within the article 100 so that the article 100 is easily handled. Additionally, a preferred power source 208 is of a sufficiently light weight to not detract from a desirable smoking experience. In some aspects, indicators are provided in varying numbers, take on different shapes, and/or are associated with an opening in the control body 200 (i.e., for release of sound when such indicators are present). Additional components of the control body 200 include but are not limited to, for example, an air intake 212, a receptacle 210 enabling electrical connection with an aerosol forming arrangement (e.g., 308) thereof, such as a resistive heating element (described below), when the cartridge 300 is attached to the control body 200, and/or a plurality of indicators at a distal end of the control body 200.

The cartridge 300 includes a housing 302 with a mouthpiece 304 having an opening 306 therethrough to allow passage of air and entrained vapor or aerosol (i.e., the components of the aerosol precursor composition in an inhalable (i.e., aerosol form)) from the cartridge 300 to a consumer during draw on the smoking article 100. The smoking article 100 is substantially rod-like or substantially tubular shaped or substantially cylindrically shaped, in particular embodiments.

The cartridge 300 further includes an aerosol forming arrangement, generally designated 308. In some aspects, the aerosol forming arrangement 308 is an atomizer (i.e., a resistive heating element 310 having a wire coil that is in electrical communication with the battery 208 and is configured to generate heat in response thereto), and an aerosol precursor composition transport element 312. In one aspect, the aerosol precursor composition transport element comprises a wick that is configured to direct the aerosol precursor composition(s) into interaction with the heat generated by the heating element 310 in order to produce the aerosol upon interaction with the heat.

Various embodiments of materials configured to produce heat when electrical current is applied therethrough are employed to form the wire coil. Example materials from which the wire coil is formed include Kanthal (FeCrAl), Nichrome, molybdenum disilicide ($MoSi_2$), molybdenum silicide (MoSi), molybdenum disilicide doped with aluminum ($Mo(Si,Al)_2$), and ceramic (e.g., a positive temperature coefficient ceramic). The aerosol precursor composition transport element 312 is also formed from a variety of materials configured to transport a liquid. For example, in some aspects, the aerosol precursor composition transport element 312 comprises cotton and/or fiberglass. Electrically conductive heater terminals (e.g., positive and negative terminals) at the opposing ends of the heating element 310 are configured to direct current flow through the heating element 310. The heater terminals are also configured for attachment to the appropriate wiring or circuit (not illustrated) to form an electrical connection between the heating element 310 and the battery 208, when the cartridge 300 is connected to the control body 200. Specifically, in some aspects, a plug 314 is positioned at a distal attachment end of the housing 302. When the cartridge 300 is connected to the control body 200, the plug 314 engages the receptacle 210 to form an electrical connection therebetween such that current controllably flows from the battery 208, through the receptacle 210 and plug 314, and to the heating element 310. In some instances, the housing 302 of the cartridge 300 is continuous across the distal end of the housing 302 such that the distal end of the cartridge 300 is substantially closed with the plug 314 protruding therefrom.

A reservoir, generally designated 316, is disposed within the housing 302 and extends longitudinally from a first end disposed toward the proximal end of the housing 302 to a second end disposed toward the distal end of the housing 302. The reservoir 316 is configured to define two or more chambers 318A-C each having an aerosol precursor composition 320A-C disposed therein. In some aspects, for example, the two or more chambers 318A-C are defined via dividers within the housing 302, the dividers separating one chamber from another. More particularly, a divider 322A-C extending longitudinally from the first end of the reservoir to the second end of the reservoir sufficiently separates each chamber 318A-C from one another within the reservoir 316. In this manner, the reservoir 316 is divided into two chambers, three chambers, four chambers, etc., based on a quantity of aerosol precursor compositions that are desired to be individually contained within the cartridge 300.

As illustrated in FIG. 2, three dividers 322A-C define three individual chambers 318A-C in the reservoir, each chamber 318A-C receiving an individual aerosol precursor 320A-C therein. Thus, in the aspect shown in FIG. 2, the reservoir 316 is configured to contain up to three aerosol precursor compositions in the defined chambers 318A-C. A first chamber 318A comprises a first aerosol precursor composition 320A and is defined by and between a first divider 322A and a second divider 322B. A second chamber 318B comprises a second aerosol precursor composition 320B and is defined by and between the second divider 322B and a third divider 322C. A third chamber 318C comprises a third aerosol precursor composition 320C and is defined by and between the first divider 322A and the third divider 322C.

In some aspects, the aerosol precursor compositions 320A-C, which also are referred to as vapor precursor compositions, each comprise one or more different components. For example, in one aspect, the aerosol precursor compositions 320A-C each include a polyhydric alcohol (e.g., glycerin, propylene glycol, or a mixture thereof), water, nicotine, natural and artificial flavors, menthol, or a mixture thereof. Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference.

In some aspects, the aerosol precursor compositions 320A-C disposed in each of the relative chambers, 318A-C, are each different aerosol precursor compositions. For example, in such instances, the first aerosol precursor composition 320A comprises a chocolate flavor, the second aerosol precursor composition 320B comprises a vanilla flavor, and the third aerosol precursor composition 320C comprises a strawberry flavor. In another example, the first aerosol precursor composition 320A comprises a 3.6% active ingredient (i.e., nicotine) aerosol precursor composition, the second aerosol precursor composition 320B comprises a 1.1% active ingredient aerosol precursor composition, and the third aerosol precursor composition 320C comprises a 0.4% active ingredient aerosol precursor composition. In a still further example, the first aerosol precursor composition 320A comprises a vegetable glycerin (VG)-based nicotine composition, the second aerosol precursor composition 320B comprises a propylene glycol (PG)-based nicotine composition, and the third aerosol precursor composition 320C comprises a peppermint flavor without nicotine.

As illustrated in FIG. 1, each of the chambers 318A-C is in fluid communication with the aerosol forming arrangement 308, which is configured to form an aerosol from any of the aerosol precursor compositions 320A-C. In some aspects, fluid communication between the aerosol forming arrangement 308 and the chambers 318A-C includes the aerosol precursor composition transport element 312, which is configured to direct the aerosol precursor compositions 320A-C into interaction with the heat generated by the heating element 310. One such example is shown in FIG. 1. As seen therein, the cartridge 300 includes a sorptive element 324 comprising layers of nonwoven fibers formed into the shape of a circular disc disposed about a portion of an interior of the housing 302 of the cartridge 300 (i.e., about the second end of the reservoir disposed toward the distal end of the housing 302). The sorptive element 324 is operably engaged between the one or more chambers 318A-C and the aerosol precursor composition transport element 312 (the wick in this embodiment) to thereby supply the aerosol precursor compositions 320A-C to the transport element 312 (i.e., the sorptive element 324 wetted with the aerosol precursor compositions 320A-C contacts the wick, wherein the wick receives and channels the aerosol precursor compositions 320A-C therealong toward the heating element 310). That is, for example, once received by the sorptive element 324, the aerosol precursor compositions 320A-C are transported by the aerosol precursor composition transport element 312, via capillary action, to an aerosolization zone 326 of the cartridge 300. As illustrated, the aerosol precursor composition transport element 312 is in direct contact with the heating element 310, and thus the aerosolization zone 326 is defined at or about the contact between the wick and the heating element 310.

In some aspects, the respective aerosol precursor compositions 320A-C of the two or more chambers 318A-C are directed to the aerosol forming arrangement 308 in substantially equal normal quantities. More particularly, in one aspect, substantially equal percentages, quantities, flow rates, etc. of each of the aerosol precursor compositions 320A-C are directed to the aerosol forming arrangement 308 so that the aerosol produced in the aerosol forming arrangement comprises equal parts of each aerosol precursor composition 320A-C. For example, the aerosol produced comprises approximately 33% of the first aerosol precursor composition 320A, approximately 33% of the second aerosol precursor composition 320B, and approximately 33% of the third aerosol precursor composition 320C. One skilled in the art will appreciate, however, that in other aspects, the normal quantities of the respective aerosol precursor compositions 320A-C are not substantially equal, but configured to be different. For example, the aerosol produced comprises approximately 30% of the first aerosol precursor composition 320A, approximately 35% of the second aerosol precursor composition 320B, and approximately 35% of the third aerosol precursor composition 320C. Accordingly, the dispensed the normal quantities of the respective aerosol precursor compositions 320A-C can vary as necessary or desired.

However, where a consumer wishes to increase a quantity of one or more specific aerosol precursor composition 320A-C so that the aerosol produced in the aerosol forming arrangement 308 comprises an increased percentage of the one or more aerosol precursor compositions (i.e., an extra charge of one of the aerosol precursor compositions), an actuator, generally designated 328, is used to direct an increased quantity of a desired one of the aerosol precursor composition(s) 320A-C from a corresponding chamber 318A-C to the aerosol forming arrangement 308. More particularly, in one aspect, the actuator 328 is engaged with the housing 302 and is configured to selectively and operably engage any one of the two or more chambers 318A-C. As illustrated, in one generic exemplary embodiment in FIG. 1, the actuator 328 is disposed at the first end of the reservoir 316 and comprises a single actuator that is engagable and independently operable with each of the two or more chambers 318A-C. However, as disclosed herein, other aspects of the disclosure also contemplate a dedicated actuator engaged and operable with each individual chamber 318A-C.

Referring now to FIGS. 3A-3C, exemplary embodiments of the actuator 328 are illustrated. These are not limiting examples, though, and it will be apparent to one of skill in the art that any type of actuator that is in fluid communication with one of the two or more chambers 318A-C, and configured to reduce a volume or increase a pressure in any one of these chambers 318A-C having the actuator engaged therewith, is contemplated.

In FIG. 3A, one aspect of a cartridge 300A for a smoking article (e.g., smoking article 100) is illustrated. As provided in FIG. 1, the cartridge 300A comprises a first chamber 318A and a second chamber 318B each having received therein any one of the aerosol precursor compositions 320A-B, respectively. Though not shown in this view for this aspect, the cartridge 300A comprises additional chambers containing additional aerosol precursor compositions. FIG. 3A illustrates one embodiment, where each of the first chamber 318A and the second chamber 318B have an individual actuator, 328A, engaged therewith. In this instance, each actuator 328A is independently actuatable. However, in alternative embodiments, a single actuator 328A is engaged with both of the first and second chambers 318A, 318B. Regardless, in the embodiment illustrated in FIG. 3A, each actuator 328A includes a flexible bulb 330 comprising an elastic material that is capable of deformation by the consumer in order to reduce a volume and thereby force air to or increase pressure in an interior of the cartridge 300A; specifically to the respective one of the chambers 318A-B.

As illustrated in FIG. 3A, in one aspect, each chamber 318A-B comprises a single bulb actuator 330 operably engaged therewith. Accordingly, the chamber 318A-B in fluid communication with the bulb 330 is configured to be responsive to actuation (i.e., depression) of the bulb 330 by reducing a volume thereof so as to dispense the increased quantity of the aerosol precursor composition 320A-B from the corresponding chamber 318A-B to the aerosol forming arrangement 308. Notably, where there are two or more chambers in the cartridge 300A, a consumer may depress more than one flexible bulb 330, each flexible bulb 330 in fluid communication with a respective chamber 318A-B, at one time in order to increase quantities of multiple aerosol precursor compositions. To return the flexible bulb 330 to its original shape, an orifice 332 is defined within the bulb, or elsewhere between the bulb and the respective chamber, in order to allow ambient air back into the interior of the chamber or the bulb actuator 330 to allow the bulb actuator 330 to revert back to its initial shape after actuation (i.e., depression). In this aspect, the increased quantity of the one or more aerosol precursor compositions 320A-B dispensed by actuation of the bulb actuator 330 results in an aerosol being produced that exhibits characteristics relative to the increased quantity of selected aerosol precursor composition 320A-B.

As shown in FIG. 3A, in one embodiment, one or more quantities of the first aerosol precursor composition 320A has been selectively directed to the aerosol forming arrangement 308 in a relatively larger quantity than the second aerosol precursor composition 320B. Therefore, the resulting aerosol produced will comprise characteristics relative to the larger quantity of the first aerosol precursor composition 320A. For example, where the first aerosol precursor composition 320A comprises a strawberry flavor and the second aerosol precursor composition 320B comprises a chocolate flavor, by increasing the quantity of the first aerosol precursor composition 320A delivered to the aerosol forming arrangement 308 the aerosol produced thereby will have a more noticeable strawberry flavor as opposed to an equal chocolate and strawberry flavor.

In FIG. 3B, another aspect of a cartridge 300B for a smoking article (e.g., smoking article 100) is illustrated. As provided in FIG. 1, the cartridge 300B comprises a first chamber 318A and a second chamber 318B each having received therein an aerosol precursor composition 320A-B, respectively. Though not shown in this view, the cartridge 300B may comprise additional chambers containing additional aerosol precursor compositions. Engaged with each of the first chamber 318A and the second chamber 318B is an actuator 328B. In this embodiment, the actuator 328B includes a pump device, such as a microelectromechanical (MEMs) pump device having a button actuator 334 that is in electrical, heat, pressure, etc., connection with a pumping structure (not shown) of the pump device 328B. As illustrated in FIG. 3B, each chamber 318A-B is in fluid communication with an individual button actuator 334, where each button actuator 334 is configured to be independently actuated or simultaneously or substantially simultaneously actuated in order to increase quantities of multiple aerosol precursor compositions delivered to the aerosol forming arrangement 308. In some non-limiting examples, the pump device 328B comprises a piezoelectric micropump, an electrostatic micropump, a thermopneumatic micropump, an electromagnetic micropump, a bimetallic micropump, an ion conductive polymer film (ICPF) micropump, a phase change micropump, a shape-memory alloy (SMA) micropump, or the like. Accordingly, the chamber 318A-B in fluid communication with the pump device 328B is configured to be responsive to actuation (i.e., depression) of the button actuator 334 associated with the pump device 328B so as to pressurize the chamber 318A-B or the aerosol precursor composition 320A-B therein, and to dispense the increased quantity of the aerosol precursor composition 320A-B from the chamber 318A-B to the aerosol forming arrangement 308.

As shown in FIG. 3B, one or more quantities of both the first aerosol precursor composition 320A and the second aerosol precursor composition 320B have been selectively directed to the aerosol forming arrangement 308. Therefore, the resulting aerosol produced will comprise characteristics relative to both the first aerosol precursor composition 320A and the second aerosol precursor composition 320B. For example, where the first aerosol precursor composition 320A comprises a composition including 1.1% of an active ingredient (i.e., nicotine) and the second aerosol precursor composition 320B comprises a composition including 2.4% of that active ingredient, the normal equal quantities of the first and second aerosol precursor compositions 320A-B delivered to the aerosol forming arrangement 308 will produce an aerosol comprising a 1.75% active ingredient composition based on an average of the active ingredient content of each composition delivered thereto. By increasing the amount of the first aerosol precursor composition 320A and the second aerosol precursor composition 320B in substantially equal quantities, the produced aerosol will retain a 1.75% active ingredient composition based on an average of the active ingredient content of each composition delivered thereto. Notably, by increasing the amount of the first aerosol precursor composition 320A dispensed, the produced aerosol will include 1.53% of the active ingredient, while by increasing the amount of the second aerosol precursor composition dispensed, the produced aerosol will include a 1.96% of the active ingredient. In some instances, this proves advantageous to consumers who wish to adjust consumption of the active ingredient overall, and may do so gradually by beginning with a normal 1.75% nicotine-based composition, and selectively increasing or reducing to a composition having a desired percentage.

In FIG. 3C, a cartridge 300C for a smoking article (e.g., smoking article 100) is illustrated. As provided in FIG. 1, the cartridge 300C comprises a first chamber 318A and a second chamber 318B each having received therein an aerosol precursor composition 320A-B, respectively. Though not shown in this view, the cartridge 300C may comprise additional chambers containing additional aerosol precursor compositions. Engaged with each of the first chamber 318A and the second chamber 318B is an actuator 328C. In this embodiment, the actuator 328C includes a piston or plunger member 336 in fluid communication with one of the two or more chambers 318A-B. As illustrated in FIG. 3C, each chamber 318A-B is in fluid communication with an individual piston member 336. The piston member 336 is actuated by a consumer pushing or pressing on a top surface of the piston in order to move the piston 336 downward toward the second end of the reservoir 316. Each piston member 336 is configured to be independently actuated or simultaneously or substantially simultaneously actuated together in order to increase quantities of multiple aerosol precursor compositions dispensed to the aerosol forming arrangement 308. Accordingly, the chamber 318A-B in fluid communication with the piston member 336 is configured to be responsive to actuation (i.e., depression) of the top surface of the piston member by the actuator so as to reduce a volume of the chamber 318A-B, and to dispense the increased quantity of the aerosol precursor composition 320A-B within the chamber to the aerosol forming arrangement 308.

As in FIG. 3C, one or more quantities of the second aerosol precursor composition 320B have been selectively directed to the aerosol forming arrangement 308. Therefore, the resulting aerosol produced will comprise primary characteristics relative to the second aerosol precursor composition 320B. For example, the first aerosol precursor composition 320A comprises a PG-based composition and the second aerosol precursor composition 320B comprises a VG-based composition. In this example, by increasing the quantity of the second aerosol precursor composition 320B delivered to the aerosol forming arrangement 308 more than the first aerosol precursor composition, the aerosol produced thereby will be primarily a VG-based aerosol (e.g., a 30 PG:70 VG aerosol). To increase the PG content of the aerosol produced, a consumer pushes the top surface of the piston member 336 engaged with the first chamber 318A and an increased quantity of the PG-based composition is directed to the aerosol forming arrangement 308, such that the aerosol produced will be a primarily PG-based aerosol (60 PG:40 VG aerosol).

In some aspects, the cartridge 300 comprises a backflow prevention device 338. FIG. 1 provides an exemplary embodiment of the backflow prevention device 338, where the backflow prevention device 338 is configured to selectively prevent backflow of the increased quantity of the aerosol precursor composition 320A-C directed from the chamber operably engaged with the actuator 328 into the others of the two or more chambers 318A-C. In reference to FIG. 4, one embodiment of the backflow prevention device 338 comprises two or more aligned discs 338A-B. One of the two or more aligned discs 338A-B is independently rotatable relative to the others, about a common axis extending therethrough, wherein the discs 338A-B are also serially disposed with respect to each other along the common axis. The common axis is an axis centrally disposed relative to a longitudinal axis of the article 100 and sometimes corresponds with the longitudinal axis. In some aspects, a flow tube 340 has a distal end in fluid communication with the aerosol forming arrangement 308 and a proximal end forming the mouthpiece element 304, and is configured to direct the aerosol from the aerosol forming arrangement 308 in response to suction applied to the mouthpiece element 304. For this purpose, the flow tube 340 defines, or is aligned or substantially aligned with, the common axis, and the two or more aligned discs 338-B are independently rotatable relative to one another about the flow tube 340 (i.e., the flow tube 340 defines the axis of rotation).

The two or more aligned discs 338A-B are disposed within the interior of the housing 302 of the cartridge 300 and are disposed relative to (i.e., between) the second end of the reservoir 316 and the aerosol forming arrangement 308. In some embodiments, for example, the first aligned disc 338A is disposed between the second end of the reservoir 316 and the second aligned disc 338B, while the second aligned disc 338B is disposed between the first aligned disc 338A and the sorptive element 324. In some aspects, the two or more aligned discs 338A-B are formed from a material similar to that of the sorptive element 324, or are formed of any other material appropriately and sufficiently capable of preventing backflow of the aerosol precursor compositions 320A-C into the reservoir 316.

FIGS. 5A-5B illustrate a top view of the first and second discs 338A-B. In FIG. 5A, the first aligned disc 338A is illustrated. A planar surface of the first aligned disc 338A defines an opening 342A disposed centrally relative to the planar surface. The first aligned disc 338A comprises dimensions that allow the disc 338A to independently rotate about the flow tube 340 (i.e., the flow tube 340 extends through the opening 342A). Additionally, the planar surface of the first disc 338A defines a plurality of dispensing ports 344A equidistantly disposed along a radius originating from the common axis. In some aspects, the dispensing ports 344A are substantially equally angularly spaced apart about the respective first disc 338A. The planar surface of the first disc 338A also defines an enhancement port 346. The enhancement port 346 is equidistantly disposed with respect to the plurality of dispensing ports 344A along the radius and is angularly spaced apart from each dispensing port 344A. More particularly, for example and as illustrated in FIG. 5A, the three dispensing ports 344A are angularly spaced apart by about 120 degrees from each other and the enhancement port 346 is disposed about 60 degrees from each of two of the dispensing ports 344A.

In FIG. 5B, the second aligned disc 338B is illustrated. A planar surface of the second aligned disc 338B defines an opening 342B disposed centrally relative to the planar surface of the first aligned disc 338B. The second aligned disc 338B comprises dimensions that allow the disc 338B to independently rotate about the flow tube 340 (i.e., the flow tube 340 extends through the opening 342B. Additionally, the planar surface of the second disc 338B defines a plurality of dispensing ports 344B equidistantly disposed along a radius originating from the common axis, and wherein the dispensing ports 344B are substantially equally angularly spaced apart about the respective second disc 338B. More particularly, for example and as illustrated in FIG. 5B, three dispensing ports 344B are angularly spaced apart by about 120 degrees from each other.

Accordingly, the dispensing ports 344A disposed on the first aligned disc 338A and the dispensing ports 344B disposed on the second aligned disc are configured to be aligned with the chambers 318A-C. More particularly, in a first embodiment, one of the discs 338A-B is rotatable such that the dispensing ports 344A of the first disc 338A correspond with the dispensing ports 344B of the second disc 338B to allow substantially equal normal quantities of the respective aerosol precursor compositions 320A-C of the two or more chambers 318A-C to be dispensed from the reservoir 316 through the dispensing ports 344A-B and directed to the aerosol forming arrangement 308.

In a second embodiment, one of the discs 338A-B is rotatable such that the enhancement port 346 corresponds with one of the dispensing ports 344B of the second disc 338B associated with one of the chambers 318A-C. In this manner, the discs 338A-B are configured to block the other dispensing ports 344B of the second disc 338B and prevent outflow of the aerosol precursor compositions from the corresponding chambers or prevent backflow of the increased quantity of the aerosol precursor composition 320A-C from the one of the chambers 318A-C having the enhancement port aligned with the dispensing port, into the other of the chambers 318A-C. In some aspects, each of the dispensing ports 344A-B and the enhancement port 346 is approximately $1/16^{th}$ of an inch in diameter. The number of dispensing ports 344A-B is variable depending on the number of chambers defined by the reservoir 316. For example, in the embodiment discussed herein, the cartridge 300 comprises three chambers 318A-C, such that there are three dispensing ports 344A-B defined by each respective disc 338A-B (see, FIGS. 5A-B). In another example, where there are four chambers, there will be four dispensing ports 344A-B defined by each respective disc 338A-B.

Thus, when the smoking article 100 is in use, and after a quantity of a certain aerosol precursor composition(s) 320A-C is delivered to the aerosol forming arrangement 308, a consumer draws on the article 100, which will then activate the heating element 310 (e.g., such as via a puff sensor), and the components for the aerosol precursor composition 320A-C are vaporized/aerosolized in the aerosolization zone 326. Drawing upon the mouthpiece element 306 of the article 100 causes ambient air to enter the air intake 212 and pass through a central opening in the receptacle 210 and the central opening in the plug 314. In the cartridge 300, the drawn air passes through the flow tube 340 and combines with the formed vapor in the aerosolization zone 326 to form an aerosol. The aerosol then draws away from the aerosolization zone 326, passes through the flow tube 340, and out the opening 306 in the mouthpiece element 304 of the article 100 for consumption by the consumer.

It is understood that a smoking article of the types disclosed herein can encompass a variety of combinations of components useful in forming the smoking article. Reference is made for example to the smoking articles disclosed in U.S. Pat. App. Pub. No. 2014/0000638 to Sebastian et al., U.S. Pat. App. Pub. No. 2013/0255702 to Griffith, Jr. et al., and U.S. Pat. No. 8,881,737 to Collett et al., the disclosures of which are incorporated herein by reference in their entirety. Further to the above, representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, a single-use cartridge for use with an electronic smoking article is disclosed in U.S. Pat. No. 8,910,639 to Chang, et al., which is incorporated herein by reference in its entirety.

The various components of a smoking article according to the present disclosure can be chosen from components described in the art and commercially available. Examples of batteries that can be used according to the disclosure are described in U.S. Pat. App. Pub. No. 2010/0028766, the disclosure of which is incorporated herein by reference in its entirety.

An exemplary mechanism that provides puff-actuation capability includes a Model 163PC01D36 silicon sensor, manufactured by the MicroSwitch division of Honeywell, Inc., Freeport, Ill. Further examples of demand-operated electrical switches employable in a heating circuit according to the present disclosure are described in U.S. Pat. No. 4,735,217 to Gerth et al., which is incorporated herein by reference in its entirety. Further description of current regulating circuits and other control components, including microcontrollers usable in the present smoking article, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

Still further components are usable in the smoking article of the present disclosure. For example, U.S. Pat. No. 5,261,424 to Sprinkel, Jr. discloses piezoelectric sensors associated with the mouth-end of a device to detect user lip activity associated with taking a draw and then employing trigger heating in response; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 by Fernando et al. discloses computer interfacing means for smoking devices to facilitate charging and allow computer control of the device; U.S. Pat. No. 8,689,804 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components usable in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. No. 8,156,944 to Hon; U.S. Pat. App. Pub. Nos. 2006/0196518 and 2009/0188490, and U.S. Pat. No. 8,375,957 to Hon; U.S. Pat. No. 8,794,231 to Thorens et al.; U.S. Pat. Nos. 8,915,254 and 8,925,555 to Monsees et al.; U.S. Pat. App. Pub. No. 2010/0024834 and U.S. Pat. No. 8,851,083 to Oglesby et al.; U.S. Pat. App. Pub. No. 2010/0307518 to Wang; and WO 2010/091593 to Hon. A variety of the materials disclosed by the foregoing documents may be incorporated into the present devices in different combinations and in various embodiments, and all of the foregoing disclosures are incorporated herein by reference in their entireties.

FIG. 6 illustrates a method flow diagram for an exemplary method, generally designated 400, for making a smoking article (e.g., smoking article 100). In a first step, 402, a reservoir (e.g., reservoir 316) is engaged into fluid communication with an aerosol forming arrangement (e.g., arrangement 308) and is configured to form an aerosol from aerosol precursor compositions (e.g., compositions 320A-C). The reservoir is disposed within a housing (e.g., housing 302) of a cartridge (e.g., cartridge 300), and defines two or more chambers (e.g., chambers 318A-C) each extending longitudinally from a first end disposed toward a proximal end of the housing to a second end disposed toward a distal end of the housing. Each of the two or more chambers are configured to have an aerosol precursor composition disposed therein, and to direct the respective aerosol precursor compositions of the two or more chambers to the aerosol forming arrangement in substantially equal normal quantities.

In step 404, an actuator (e.g., actuator 328) is engaged with the housing such that the actuator selectively and operably engages any one of the two or more chambers defined by the reservoir. The actuator is configured to be actuatable to direct an increased quantity of the aerosol precursor composition from the chamber engaged therewith to the aerosol forming arrangement, with the increased quantity being greater than the normal quantity of the aerosol precursor composition Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A smoking article, comprising:
a control body; and
a cartridge engaged with the control body, the cartridge comprising:
a housing having a proximal end and an opposing distal end engagable with the control body;
a reservoir disposed within the housing and extending longitudinally from a first end disposed toward the proximal end of the housing to a second end disposed toward the distal end of the housing, the reservoir defining two or more chambers each having an aerosol precursor composition disposed therein, and being in fluid communication with an aerosol forming arrangement configured to form an aerosol from any of the aerosol precursor compositions, the respective aerosol precursor compositions of the two or more chambers being directed to the aerosol forming arrangement in substantially equal normal quantities; and
an actuator engaged with the housing and configured to selectively and operably engage any one of the two or more chambers defined by the reservoir, the actuator, upon actuation thereof, being configured to direct an increased quantity of the aerosol precursor composition from the chamber engaged therewith to the aerosol forming arrangement, the increased quantity being greater than the normal quantity of the aerosol precursor composition.

2. The smoking article according to claim 1, wherein the cartridge further comprises a backflow prevention device configured to selectively prevent backflow of the increased quantity of the aerosol precursor composition directed from the chamber operably engaged with the actuator into the others of the two or more chambers of the reservoir.

3. The smoking article according to claim 2, wherein the backflow prevention mechanism comprises two or more aligned discs, one of the discs being independently rotatable relative to the others, about a common axis extending therethrough, the discs being serially disposed with respect to each other along the common axis.

4. The smoking article according to claim 3, wherein a first disc and a second disc of the two or more discs each define a plurality of dispensing ports, each of the dispensing ports corresponding to the two or more chambers, and wherein rotation of the one of the discs such that the dispensing ports of the first disc correspond with the dispensing ports of the second disc allows the substantially equal normal quantities of the respective aerosol precursor compositions of the two or more chambers to be dispensed from the reservoir through the dispensing ports and directed to the aerosol forming arrangement.

5. The smoking article according to claim 4, wherein the dispensing ports of the first and second discs are equidistantly disposed along a radius originating from the common axis, and wherein the dispensing ports are substantially equally angularly spaced apart about the respective first and second disc.

6. The smoking article according to claim 5, wherein the first disc defines an enhancement port equidistantly disposed with respect to the dispensing ports along the radius and angularly spaced apart from each dispensing port such that the first disc, upon rotation thereof such that the enhancement port corresponds with one of the dispensing ports of the second disc associated with one of the chambers, blocks the other dispensing ports of the second disc and prevents backflow of the increased quantity of the aerosol precursor composition from the one of the chambers into the other of the chambers.

7. The smoking article according to claim 6, wherein the first and second discs each define three dispensing ports, the three dispensing ports being angularly spaced apart by about 120 degrees from each other, and wherein the first disc defines the enhancement port between two of the dispensing ports, such that the enhancement port is disposed about 60 degrees from each of the two of the dispensing ports.

8. The smoking article according to claim 1, wherein the actuator comprises a flexible bulb in fluid communication with one of the two or more chambers, the chamber in fluid communication with the bulb being configured to be responsive to actuation of the bulb by reducing a volume thereof so as to dispense the increased quantity of the aerosol precursor composition within the chamber to the aerosol forming arrangement.

9. The smoking article according to claim 1, wherein the actuator is in communication with a pump device, with the pump device being in fluid communication with one of the two or more chambers, the chamber in fluid communication with the pump device being configured to be responsive to actuation of the pump device by the actuator so as to pressurize the chamber or the aerosol precursor composition therein, and to dispense the increased quantity of the aerosol precursor composition within the chamber to the aerosol forming arrangement.

10. The smoking article according to claim 1, wherein the actuator is in communication with a piston member, with the piston member being in fluid communication with one of the two or more chambers, the chamber in fluid communication with the piston member being configured to be responsive to actuation of the piston member by the actuator so as to reduce a volume of the chamber, and to dispense the increased quantity of the aerosol precursor composition within the chamber to the aerosol forming arrangement.

11. The smoking article according to claim 1, wherein the control body comprises a control component, a flow sensor, and a battery, and wherein the aerosol forming arrangement includes a resistive heating element in electrical communication with the battery and configured to generate heat in response thereto, the aerosol precursor compositions directed to the aerosol forming arrangement producing the aerosol upon interaction with the heat generated by the heating element.

12. The smoking article according to claim 11, comprising a transport element configured to direct the aerosol precursor compositions into interaction with the heat generated by the heating element, and a sorptive element operably engaged between the one or more chambers and the transport element, the sorptive element being configured to sorptively receive the aerosol precursor compositions, and to supply the aerosol precursor compositions to the transport element.

13. The smoking article according to claim 1, wherein the cartridge defines a flow tube having a proximal end forming a mouthpiece element, the flow tube extending between the two or more chambers to a distal end in fluid communication with the aerosol forming arrangement so as to direct the aerosol therefrom through the mouthpiece element in response to suction applied to the mouthpiece element.

14. The smoking article according to claim 1, wherein each of the two or more chambers includes a different flavor, a different percentage of an active ingredient, or a different composition of the aerosol precursor composition.

15. A cartridge for a smoking article, comprising:

a housing having a proximal end and an opposing distal end engagable with a control body of the smoking article;

a reservoir disposed within the housing and extending longitudinally from a first end disposed toward the proximal end of the housing to a second end disposed toward the distal end of the housing, the reservoir defining two or more chambers each having an aerosol precursor composition disposed therein, and being in fluid communication with an aerosol forming arrangement configured to form an aerosol from any of the aerosol precursor compositions, the respective aerosol precursor compositions of the two or more chambers being directed to the aerosol forming arrangement in substantially equal normal quantities; and an actuator engaged with the housing and configured to selectively and operably engage any one of the two or more chambers defined by the reservoir, the actuator, upon actuation thereof, being configured to direct an increased quantity of the aerosol precursor composition from the chamber engaged therewith to the aerosol forming arrangement, the increased quantity being greater than the normal quantity of the aerosol precursor composition.

16. The cartridge according to claim 15, comprising a backflow prevention device configured to selectively prevent backflow of the increased quantity of the aerosol precursor composition directed from the chamber operably engaged with the actuator into the others of the two or more chambers of the reservoir.

17. The cartridge according to claim 16, wherein the backflow prevention mechanism comprises two or more aligned discs, one of the discs being independently rotatable relative to the others, about a common axis extending therethrough, the discs being serially disposed with respect to each other along the common axis.

18. The cartridge according to claim 17, wherein a first disc and a second disc of the two or more discs each define a plurality of dispensing ports, each of the dispensing ports corresponding to the two or more chambers, and wherein rotation of the one of the discs such that the dispensing ports of the first disc correspond with the dispensing ports of the second disc allows the substantially equal normal quantities of the respective aerosol precursor compositions of the two or more chambers to be dispensed from the reservoir through the dispensing ports and directed to the aerosol forming arrangement.

19. The cartridge according to claim 18, wherein the dispensing ports of the first and second discs are equidistantly disposed along a radius originating from the common axis, and wherein the dispensing ports are substantially equally angularly spaced apart about the respective first and second disc.

20. The cartridge according to claim 19, wherein the first disc defines an enhancement port equidistantly disposed with respect to the dispensing ports along the radius and angularly spaced apart from each dispensing port such that the first disc, upon rotation thereof such that the enhancement port corresponds with one of the dispensing ports of the second disc associated with one of the chambers, blocks the other dispensing ports of the second disc and prevents backflow of the increased quantity of the aerosol precursor composition from the one of the chambers into the other of the chambers.

21. The cartridge according to claim 20, wherein the first and second discs each define three dispensing ports, the three dispensing ports being angularly spaced apart by about 120 degrees from each other, and wherein the first disc defines the enhancement port between two of the dispensing ports, such that the enhancement port is disposed about 60 degrees from each of the two of the dispensing ports.

22. The cartridge according to claim 15, wherein the actuator comprises a flexible bulb in fluid communication with one of the two or more chambers, the chamber in fluid communication with the bulb being configured to be responsive to actuation of the bulb by reducing a volume thereof so as to dispense the increased quantity of the aerosol precursor composition within the chamber to the aerosol forming arrangement.

23. The cartridge according to claim 15, wherein the actuator is in communication with a pump device, with the pump device being in fluid communication with one of the two or more chambers, the chamber in fluid communication with the pump device being configured to be responsive to actuation of the pump device by the actuator so as to pressurize the chamber or the aerosol precursor composition therein, and to dispense the increased quantity of the aerosol precursor composition within the chamber to the aerosol forming arrangement.

24. The cartridge according to claim 15, wherein the actuator is in communication with a piston member, with the piston member being in fluid communication with one of the two or more chambers, the chamber in fluid communication with the piston member being configured to be responsive to actuation of the piston member by the actuator so as to reduce a volume of the chamber, and to dispense the increased quantity of the aerosol precursor composition within the chamber to the aerosol forming arrangement.

25. The cartridge according to claim 15, wherein the aerosol forming arrangement includes a resistive heating element in electrical communication with a battery and configured to generate heat in response thereto, the aerosol precursor compositions directed to the aerosol forming arrangement producing the aerosol upon interaction with the heat generated by the heating element.

26. The cartridge according to claim 25, wherein the aerosol forming arrangement includes a transport element configured to direct the aerosol precursor compositions into interaction with the heat generated by the heating element, and a sorptive element operably engaged between the one or more chambers and the transport element, the sorptive element being configured to sorptively receive the aerosol precursor compositions, and to supply the aerosol precursor compositions to the transport element.

27. The cartridge according to claim 15, wherein the housing defines a flow tube having a proximal end forming a mouthpiece element, the flow tube extending between the two or more chambers to a distal end in fluid communication with the aerosol forming arrangement so as to direct the aerosol therefrom through the mouthpiece element in response to suction applied to the mouthpiece element.

28. The cartridge according to claim 15, wherein each of the two or more chambers includes a different flavor, a different percentage of an active ingredient, or a different composition of the aerosol precursor composition.

29. A method for making a smoking article, comprising:

engaging a reservoir into fluid communication with an aerosol forming arrangement configured to form an aerosol from aerosol precursor compositions, the reservoir being disposed within a housing of a cartridge, and defining two or more chambers each extending longitudinally from a first end disposed toward a proximal end of the housing to a second end disposed toward a distal end of the housing, each of the two or more chambers being configured to have an aerosol precursor composition disposed therein, and to direct the respective aerosol precursor compositions of the two or more chambers to the aerosol forming arrangement in substantially equal normal quantities; and engaging an actuator with the housing such that the actuator selectively and operably engages any one of the two or more chambers defined by the reservoir, the actuator being configured to be actuatable to direct an increased quantity of the aerosol precursor composition from the chamber engaged therewith to the aerosol forming arrangement, with the increased quantity being greater than the normal quantity of the aerosol precursor composition.

30. The method according to claim 29, comprising engaging the proximal end or the distal end of the housing of the cartridge with a control body.

31. The method according to claim 29, comprising engaging a backflow prevention device between the reservoir and the aerosol forming arrangement and within the housing, the backflow prevention device being configured to selectively prevent backflow of the increased quantity of the aerosol precursor composition directed from the chamber operably engaged with the actuator into the others of the two or more chambers of the reservoir.

32. The method according to claim 31, wherein engaging a backflow prevention device comprises engaging two or more discs, aligned along a common axis extending therethrough and serially disposed with respect to each other, between the reservoir and the aerosol forming arrangement, one of the discs being independently rotatable relative to the others.

33. The method according to claim 32, wherein engaging two or more discs comprises serially aligning first and second discs along the common axis thereof and with respect to each other such that one of the first and second discs is rotatable relative to the other of the first and second discs, wherein each of the first and second discs defines a plurality of dispensing ports, with each of the dispensing ports corresponding to one of the two or more chambers, and wherein rotation of the one of the discs such that the dispensing ports of the first disc correspond with the dispensing ports of the second disc allows the substantially equal normal quantities of the respective aerosol precursor compositions of the two or more chambers to be dispensed from the reservoir through the dispensing ports and directed to the aerosol forming arrangement.

34. The method according to claim 33, comprising forming the dispensing ports in each of the first and second discs such that the dispensing ports are equidistantly disposed along a radius originating from the common axis, and such that the dispensing ports are substantially equally angularly spaced apart about the respective first and second disc.

35. The method according to claim 34, comprising forming an enhancement port in the first disc, the enhancement port being equidistantly disposed, with respect to the dispensing ports, along the radius and being angularly spaced apart from each dispensing port such that the first disc, upon rotation thereof such that the enhancement port corresponds with one of the dispensing ports of the second disc associated with one of the chambers, blocks the other dispensing ports of the second disc and prevents backflow of the increased quantity of the aerosol precursor composition from the one of the chambers into the other of the chambers.

36. The method according to claim 35, comprising forming three dispensing ports in each of the first and second discs such that the three dispensing ports are angularly spaced apart by about 120 degrees from each other, and forming the enhancement port in the first disc, between two of the dispensing ports, such that the enhancement port is disposed about 60 degrees from each of the two of the dispensing ports.

37. The method according to claim 29, wherein engaging the actuator comprises engaging a flexible bulb with the housing and in fluid communication with one of the two or more chambers, such that actuation of the bulb reduces a volume of the one of two or more chambers so as to dispense the increased quantity of the aerosol precursor composition from the chamber to the aerosol forming arrangement.

38. The method according to claim 29, wherein engaging the actuator comprises engaging the actuator in communication with a pump device in fluid communication with one of the two or more chambers, such that actuation of the pump device by the actuator pressurizes the one of the two or more chambers or the aerosol precursor composition therein so as to dispense the increased quantity of the aerosol precursor composition from the chamber to the aerosol forming arrangement.

39. The method according to claim 29, wherein engaging the actuator comprises engaging the actuator in communication with a piston member in fluid communication with one of the two or more chambers, such that actuation of the piston member by the actuator reduces a volume of the one of the two or more chambers so as to dispense the increased quantity of the aerosol precursor composition from the chamber to the aerosol forming arrangement.

40. The method according to claim 30, wherein engaging the housing of the cartridge with a control body comprises engaging the control body comprising a control component, a flow sensor, and a battery, wherein the aerosol forming arrangement includes a resistive heating element, such that the resistive heating element is electrically communicable with the battery to generate heat in response thereto, and such that the aerosol forming arrangement produces the aerosol upon interaction of the aerosol precursor compositions directed thereto with the heat generated by the heating element.

41. The method according to claim 40, comprising operably engaging a sorptive element between the one or more chambers and a transport element disposed within the housing, wherein the transport element is configured to direct the aerosol precursor compositions into interaction with the heat generated by the heating element, and wherein the sorptive element is configured to sorptively receive the aerosol precursor compositions, and to supply the aerosol precursor compositions to the transport element.

42. The method according to claim 29, comprising engaging a flow tube having a proximal end forming a mouthpiece element between the two or more chambers of the housing, such that a distal end thereof is in fluid communication with the aerosol forming arrangement, the flow tube being configured to direct the aerosol from the aerosol forming arrangement and through the mouthpiece element in response to suction applied to the mouthpiece element.

43. The method according to claim 29, comprising introducing a different flavor, a different percentage of an active ingredient, or a different composition of the aerosol precursor composition in each of the two or more chambers.

* * * * *